US011471392B2

(12) United States Patent
Wunsch et al.

(10) Patent No.: US 11,471,392 B2
(45) Date of Patent: Oct. 18, 2022

(54) OXIDIZING COMPOSITION COMPRISING AN OXYALKYLENATED FATTY ALCOHOL AND AN OXYALYKLENATED FATTY AMIDE

(71) Applicant: L'OREAL, Paris (FR)

(72) Inventors: Karl Wunsch, Saint-Ouen (FR); Agathe Lahaye, Saint-Ouen (FR); Dominique Leptacz, Chevilly la Rue (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 17/414,259

(22) PCT Filed: Dec. 16, 2019

(86) PCT No.: PCT/EP2019/085413
§ 371 (c)(1),
(2) Date: Jun. 15, 2021

(87) PCT Pub. No.: WO2020/127092
PCT Pub. Date: Jun. 25, 2020

(65) Prior Publication Data
US 2022/0047480 A1 Feb. 17, 2022

(30) Foreign Application Priority Data

Dec. 17, 2018 (FR) ........................ 1873096

(51) Int. Cl.
| | | |
|---|---|---|
| *A61Q 5/08* | (2006.01) | |
| *A61K 8/42* | (2006.01) | |
| *A61K 8/39* | (2006.01) | |
| *A61Q 5/04* | (2006.01) | |
| *A61Q 5/10* | (2006.01) | |

(52) U.S. Cl.
CPC .............. *A61K 8/42* (2013.01); *A61K 8/39* (2013.01); *A61Q 5/04* (2013.01); *A61Q 5/08* (2013.01); *A61Q 5/10* (2013.01); *A61K 2800/4322* (2013.01); *A61K 2800/4324* (2013.01)

(58) Field of Classification Search
CPC ... A61Q 5/08; A61Q 5/10; A61K 8/22; A61K 2800/882; A61K 8/342; A61K 2800/4322; A61K 2800/4324; A61K 2800/884; A61K 8/34; A61K 8/42; A61K 8/39
USPC ......................................... 424/62
See application file for complete search history.

(56) References Cited

U.S. PATENT DOCUMENTS

| | | |
|---|---|---|
| 6,692,539 B2 | 2/2004 | Desenne et al. |
| 8,142,518 B2 | 3/2012 | Deconinck et al. |
| 8,814,951 B2 | 8/2014 | Goget et al. |
| 9,066,890 B2 | 6/2015 | Charrier et al. |
| 2004/0205904 A1 | 10/2004 | Cotteret et al. |
| 2005/0025736 A1 | 2/2005 | Jachowicz et al. |
| 2005/0125912 A1 | 6/2005 | Desenne et al. |
| 2010/0158844 A1* | 6/2010 | Braida-Valerio ........ A61K 8/86 424/70.1 |
| 2010/0275387 A1* | 11/2010 | Charrier ................. A61K 8/585 8/408 |
| 2011/0155167 A1* | 6/2011 | Deconinck ............... A61K 8/31 8/408 |
| 2014/0090185 A1 | 4/2014 | Benn |
| 2015/0056151 A1* | 2/2015 | Deconinck ............... A61K 8/31 206/581 |
| 2022/0047480 A1 | 2/2022 | Wunsch et al. |

FOREIGN PATENT DOCUMENTS

| | | |
|---|---|---|
| BR | 112021011575-7 A2 | 8/2021 |
| CN | 113164338 A | 7/2021 |
| EP | 1329216 A1 | 7/2003 |
| EP | 1428517 A1 | 6/2004 |
| EP | 2338572 A1 | 6/2011 |
| EP | 3897528 A1 | 10/2021 |
| FR | 2968206 A1 | 6/2012 |
| FR | 3089799 A1 | 6/2020 |
| JP | 2003-192551 A | 7/2003 |
| JP | 2011-132240 A | 7/2011 |
| JP | 2013-544862 A | 12/2013 |
| JP | 2014-518242 A | 7/2014 |
| JP | 2022-511956 A | 2/2022 |
| KR | 10-2021-0090237 A | 7/2021 |
| WO | 2020/127092 A1 | 6/2020 |

OTHER PUBLICATIONS

Stic Search Report dated Jan. 11, 2022.*
International Search Report and Written Opinion for counterpart Application No. PCT/EP2019/085413, dated Feb. 5, 2020.

* cited by examiner

*Primary Examiner* — Eisa B Elhilo
(74) *Attorney, Agent, or Firm* — The Marbury Law Group, PLLC

(57) ABSTRACT

The subject of the invention is a composition for treating keratin fibers, comprising one or more oxyalkylenated fatty amide(s) of formula (I), one or more oxyalkylenated fatty alcohol(s), and one or more chemical oxidizing agent(s); it being understood that the oxyethylenated fatty alcohol(s)/oxyethylenated fatty amide(s) of formula (I) weight ratio is less than or equal to 1 and that the pH of the composition is less than or equal to 5.

19 Claims, No Drawings

OXIDIZING COMPOSITION COMPRISING AN OXYALKYLENATED FATTY ALCOHOL AND AN OXYALYKLENATED FATTY AMIDE

CROSS REFERENCE TO RELATED APPLICATION

This is a national stage application of PCT/EP2019/085413, filed internationally on Dec. 16, 2019, which claims priority to French Application No. 1873096, filed on Dec. 17, 2018, both of which are incorporated by reference herein in their entireties.

The subject of the present invention is a composition for treating human keratin fibers such as the hair, comprising one or more particular oxyalkylenated (OA) fatty amide(s); one or more oxyalkylenated fatty alcohol(s); and one or more chemical oxidizing agent (s); the pH of the composition being less than or equal to 5.

In cosmetics, oxidizing compositions are used in the fields of dyeing, bleaching and permanently transforming or reshaping keratin fibers, and in particular human keratin fibers such as the hair.

Thus, in the oxidation dyeing of hair, oxidizing compositions are mixed with oxidation dyes (bases and couplers), which are colorless by themselves, to generate compounds that are colored and coloring by a process of oxidative condensation. Oxidizing compositions are also used in the direct dyeing of the hair as a mixture with certain direct dyes that are colored and coloring, in order to obtain a coloring with a lightening effect on the hair. Among the oxidizing agents conventionally used for dyeing keratin fibers, mention may be made of hydrogen peroxide or compounds capable of producing hydrogen peroxide by hydrolysis, such as urea peroxide, and persalts such as perborates and persulfates, hydrogen peroxide being more particularly preferred.

In hair bleaching, bleaching compositions contain one or more oxidizing agents. Among these oxidizing agents, the ones most conventionally used are hydrogen peroxide or compounds that are capable of producing hydrogen peroxide by hydrolysis, such as urea peroxide or persalts such as perborates, percarbonates and persulfates, hydrogen peroxide and persulfates being particularly preferred.

These compositions may be aqueous compositions containing alkaline agents (amines or aqueous ammonia) that are diluted at the time of use with an aqueous hydrogen peroxide composition.

These compositions may also be formed from anhydrous products that contain alkaline compounds (amines and alkaline silicates), and a peroxygenated reagent such as ammonium or alkali metal persulfates, perborates or percarbonates, which is diluted at the time of use with an aqueous hydrogen peroxide composition.

Permanently reshaping the hair consists, in a first step, in opening the —S—S-disulfide bonds of keratin (cystine) using a composition containing a suitable reducing agent (reduction step), and then, after having rinsed the head of hair thus treated, in reconstituting the disulfide bonds, in a second step, by applying to the hair, which has been placed under tension beforehand (curlers and others), an oxidizing composition (oxidation step, also known as fixing step) so as finally to give the hair the desired shape. This technique thus makes it possible, without preference, either to make the hair wavy or to relax or uncurl it. The new shape given to the hair by a chemical treatment such as that above is eminently long-lasting and especially withstands washing with water or shampoo washes, as opposed to the simple standard techniques of temporary reshaping, such as hair setting.

The oxidizing compositions required for performing the fixing step are usually compositions based on aqueous hydrogen peroxide solution. It is sought to obtain compositions that are ever more effective, in particular in terms of lightening or bleaching, while respecting as far as possible the integrity of the keratin fibers and giving said fibers the best possible cosmetic properties.

The oxidizing compositions required for performing the fixing step are usually compositions based on aqueous hydrogen peroxide solution. It is sought to obtain compositions that are ever more effective, in particular in terms of lightening or bleaching, while respecting as far as possible the integrity of the keratin fibers and giving said fibers the best possible cosmetic properties.

The aim of the present invention is to provide novel oxidizing compositions which make it possible to improve the dyeing and/or lightening properties of the dyeing and/or bleaching compositions and which are stable over time, in particular stable with respect to cold.

This aim is achieved with the present invention, a subject of which is a composition comprising:
one or more oxyalkylenated fatty amides of formula (I) as described below;
one or more oxyalkylenated fatty alcohols; and
one or more chemical oxidizing agent(s);
the oxyalkylenated fatty alcohols/oxyalkylenated fatty amides of formula (I) weight ratio being less than or equal to 1
and
the pH of the composition being less than or equal to 5.

The composition of the invention is especially intended for treating keratin fibers, in particular human keratin fibers such as the hair.

When the composition in accordance with the invention is used for dyeing keratin fibers, good dyeing properties are obtained, especially powerful, chromatic and sparingly selective colorings that show good resistance to the various attacks to which the hair may be subjected, such as shampoo washes, light, sweat and permanent reshaping operations, without impairing the cosmetic properties of the keratin fibers.

The composition in accordance with the present invention makes it possible to obtain a good effect of lightening keratin fibers without damaging them and without impairing their cosmetic properties, in particular when it is used for bleaching.

Furthermore, the composition in accordance with the invention shows good stability over time, especially with respect to storage at low temperatures, for example at temperatures of less than 4° C.

A subject of the invention is also a process for treating keratin fibers, in particular a process for dyeing or bleaching keratin fibers, using this oxidizing composition.

Another subject of the invention is the use of this oxidizing composition for the treatment of keratin fibers, in particular the dyeing or bleaching of keratin fibers.

In the text hereinbelow, unless otherwise indicated, the limits of the indicated ranges are included in the invention.

The term "at least one" is intended to mean "one or more".

The term "stable" is intended to mean a composition which does not show any significant change in appearance, odor, pH and/or rheology after storage, in particular after storage for 2 months at 4° C. Among the changes in appearance, mention may in particular be made of phase separation, precipitation and creaming.

OA Fatty Amide

The oxyalkylenated fatty amide(s) according to the invention is (are) chosen from the compounds of formula (I) below:

$$R—CO—N(R')-(Alk-O)_nH \quad (I)$$

wherein:

R denotes an optionally substituted $C_8$-$C_{30}$, preferably $C_{10}$-$C_{24}$ and better still $C_{12}$-$C_{22}$ alkyl or alkenyl radical, R' denotes a hydrogen atom or an $(Alk-O)_mH$ radical, and preferably a hydrogen atom, Alk denotes a divalent alkylene radical comprising from 1 to 8 carbon atoms, preferably 2 or 3 carbon atoms, n, m denote, independently of one another, a number ranging from 1 to 50, preferably from 1 to 20, better still from 1 to 10.

Preferably, the oxyalkylenated fatty amide(s) according to the invention is (are) chosen from the oxyethylenated fatty amides of formula (I') below:

$$R—CO—N(R')—(CH_2CH_2O)_nH \quad (I')$$

wherein:

R denotes an optionally substituted $C_8$-$C_{30}$, preferably $C_{10}$-$C_{30}$ and better still $C_{12}$-$C_{22}$ alkyl or alkenyl radical, R' denotes a hydrogen atom or a $(CH_2CH_2O)_mH$ radical, and preferably a hydrogen atom, n, m denote, independently of one another, a number ranging from 1 to 50, preferably from 1 to 20, better still from 1 to 10.

Particularly preferably, the oxyalkylenated fatty amide(s) according to the invention is (are) chosen from the oxyalkylenated fatty amides of formula (I') wherein R' represents a hydrogen atom, R denotes a $C_{12}$-$C_{22}$ alkyl or alkenyl radical and n denotes a number ranging from 2 to 5.

Among the compounds of formula (I'), oxyalkylenated rapeseed acid amides are preferred, such as the compound having the INCI name PEG-4 rapeseedamide, sold in particular under the name Amidet® N by the company Kao.

The composition in accordance with the invention generally has a total content of oxyalkylenated fatty amide(s) of formula (I) ranging from 0.1% to 5% by weight, preferably from 0.5% to 4% by weight, more preferentially from 0.8% to 3% by weight, relative to the total weight of the composition.

In one preferred embodiment, the composition according to the invention has a total content of oxyalkylenated fatty amide(s) of formula (I') ranging from 0.1% to 5% by weight, preferably from 0.5% to 4% by weight, more preferentially from 0.8% to 3% by weight, relative to the total weight of the composition.

In the composition in accordance with the invention, the weight ratio between the total content of oxyalkylenated fatty alcohol(s) and the total content of oxyalkylenated fatty amide(s) of formula (I) is less than or equal to 1, preferably less than 1, preferentially less than or equal to 0.9, more preferentially from 0.9 to 0.1, even more preferentially from 0.8 to 0.5.

OA Fatty Alcohol

The term "fatty alcohol" means a long-chain aliphatic alcohol comprising from 8 to 30 carbon atoms and comprising at least one hydroxyl group OH. The fatty alcohols according to the invention are oxyalkylenated (OA). They may comprise from 1 to 50 oxyalkylenated groups. The oxyalkylenated groups may be chosen from oxyethylenated (OE) or oxypropylenated (OP) groups, preferably OE groups.

The oxyalkylenated fatty alcohols may be saturated or unsaturated, and linear or branched, and comprise from 8 to 30 carbon atoms. Preferably, the oxyalkylenated fatty alcohols have the structure $R-(AlkO)_pH$ with R denoting a linear alkyl group which is optionally substituted with one or more hydroxyl groups, comprising from 8 to 30, better still from 10 to 28, or even from 12 to 24 atoms, even better still from 14 to 22 carbon atoms, Alk represents a divalent alkylene radical comprising from 1 to 6 carbon atoms, preferably from 1 to 4 carbon atoms, preferentially 2 to 3 carbon atoms, p represents a number ranging from 1 to 50, preferably from 2 to 40, preferentially from 10 to 35, better still from 15 to 30. More preferably, Alk is a —$CH_2CH_2$— radical.

Preferably, the oxyalkylenated fatty alcohols comprise at least 10 oxyalkylenated units. They may in particular have a number of oxyalkylene groups, preferably oxyethylene groups, ranging from 10 to 50, preferably from 10 to 35 and even more preferably from 15 to 30, such as for example the products of addition of ethylene oxide and of stearyl alcohol or cetyl alcohol.

The oxyalkylenated, preferably oxyethylenated, fatty alcohols according to the invention may be chosen from oxyethylenated cetyl alcohol, oxyethylenated oleyl alcohol, oxyethylenated oleocetyl alcohol, oxyethylenated behenyl alcohol, oxyethylenated cetearyl alcohol, oxyethylenated stearyl alcohol, and mixtures thereof, and more preferably from oxyethylenated stearyl alcohol, oxyethylenated cetyl alcohol and oxyethylenated cetearyl alcohol. Preferably, the oxyalkylenated fatty alcohol is chosen from stearyl alcohol 20 OE (CTFA name steareth-20) and cetearyl alcohol 25 OE (CTFA name ceteareth-25).

As compounds of oxyalkylenated fatty alcohol type, mention may especially be made of the following products on the market:

Mergital LM2 (Cognis) [lauryl alcohol 2 OE];
Ifralan L12 (Ifrachem) and Rewopal 12 (Goldschmidt) [lauryl alcohol 12 OE];
Empilan KA 2.5/90FL (Albright & Wilson) and Mergital BL309 (Cognis) [decyl alcohol 3 OE];
Empilan KA 5/90FL (Albright & Wilson) and Mergital BL589 (Cognis) [decyl alcohol 5 OE];
Brij 58 (Uniquema) and Simulsol 58 (SEPPIC) [cetyl alcohol 20 OE];
Emulgin 05 (Cognis) [oleocetyl alcohol 5 OE];
Mergital OC30 (Cognis) [oleocetyl alcohol 30 OE];
Brij 72 (Uniquema) [stearyl alcohol 2 OE];
Brij 76 (Uniquema) [stearyl alcohol 10 OE];
Brij 78P (Uniquema) [stearyl alcohol 20 OE];
Brij 700 (Uniquema) [stearyl alcohol 100 OE];
Eumulgin B1 (Cognis) [cetylstearyl alcohol 12 OE];
Eumulgin L (Cognis) [cetyll alcohol 9 OE and 20P];
Eumulgin B 25 (BASF) [cetylstearyl alcohol 25 OE];
Witconol APM (Goldschmidt) [myristyl alcohol 3 OP].

According to one embodiment, the composition comprises at least two different oxyalkylenated fatty alcohols, preferably at least two different oxyethylenated fatty alcohols. These oxyalkylenated, preferably oxyethylenated, fatty alcohols may be chosen from the list above, preferably stearyl alcohol 20 OE and cetylstearyl alcohol 25 OE.

The composition in accordance with the invention generally has a total content of oxyalkylenated fatty alcohol(s) ranging from 0.1% to 5% by weight, preferably from 0.2% to 4% by weight, preferentially from 0.3% to 3% by weight, better still from 0.5% to 2% by weight, relative to the total weight of the composition.

In one preferred embodiment, the composition in accordance with the invention has a total content of oxyethylenated fatty alcohol(s) ranging from 0.1% to 5% by weight, preferably from 0.2% to 4% by weight, preferentially from 0.3% to 3% by weight, better still from 0.5% to 2% by weight, relative to the total weight of the composition.

Chemical Oxidizing Agent

The composition of the invention comprises one or more chemical oxidizing agent(s). The term "chemical oxidizing agent" is intended to mean an oxidizing agent other than atmospheric oxygen.

More particularly, the chemical oxidizing agent(s) is (are) chosen from hydrogen peroxide, urea peroxide, alkali metal bromates, peroxygenated salts, for instance persulfates or perborates, peracids and precursors thereof and alkali metal or alkaline-earth metal percarbonates.

The chemical oxidizing agent is advantageously hydrogen peroxide.

The concentration of chemical oxidizing agent(s) may range more particularly from 0.1% to 50% by weight, even more preferentially from 0.5% to 30% by weight and better still from 1')/0 to 20% by weight relative to the weight of the composition.

The pH of the oxidizing composition according to the invention is less than or equal to 5.

The pH of the oxidizing composition according to the invention generally ranges from 1.5 to 4.5 and preferably from 2 to 3.5. It may be adjusted by adding acidifying agents such as hydrochloric acid, acetic acid, lactic acid, boric acid, citric acid or phosphoric acid or acidifying agents in the presence of alkaline agents.

The composition according to the invention may comprise one or more fatty substances, other than the oxyalkylenated fatty amides of formula (I) and than the oxyalkylenated fatty alcohols described above, which are preferably solid.

The term "fatty substance" is intended to mean an organic compound that is insoluble in water at ambient temperature (25° C.) and at atmospheric pressure (1 atm), i.e. which has a solubility of less than 5% by weight, preferably less than 1 by weight. They bear in their structure at least one hydrocarbon-based chain including at least 6 carbon atoms or a sequence of at least two siloxane groups. In addition, the fatty substances are generally soluble, under the same temperature and pressure conditions, in organic solvents such as chloroform, ethanol, benzene, liquid petroleum jelly or decamethylcyclopentasiloxane.

The term "solid fatty substance" is intended to mean a fatty substance that is solid at ambient temperature and atmospheric pressure (25° C., 1 atm); they preferably have a viscosity of greater than 2 Pa·s, measured at 25° C. and at a shear rate of 1 s$^{-1}$.

The term "oil" or "liquid fatty substance" is intended to mean a fatty substance that is liquid at ambient temperature (25° C.) and at atmospheric pressure (760 mmHg or 1 atm).

According to one embodiment, the fatty substances in the composition may be solid or liquid.

Preferably, the fatty substance(s) other than the oxyalkylenated fatty amides of formula (I) and other than the oxyalkylenated fatty alcohols according to the invention does (do) not comprise any oxyalkylenated units. Preferably, they do not contain any glycerol units. More particularly, the fatty substances are other than fatty acids.

The fatty substances may be chosen from $C_6$-$C_{16}$ hydrocarbons, hydrocarbons comprising more than 16 carbon atoms, non-silicone oils of animal origin, triglycerides of plant or synthetic origin, fatty alcohols, fatty acid and/or fatty alcohol esters, or mixtures thereof.

As an examples of suitable fatty alcohols, mention may also be made of octyldodecanol, 2-butyloctanol, 2-hexyldecanol, 2-undecylpentadecanol, oleyl alcohol, linolenyl alcohol, ricinoleyl alcohol, undecylenyl alcohol, linoleyl alcohol, cetyl alcohol, stearyl alcohol, cetearyl alcohol, behenyl alcohol, and mixtures thereof.

According to one particular embodiment, the composition comprises at least one fatty alcohol other than the oxyalkylenated fatty alcohols, which is preferably solid, chosen from cetyl alcohol, stearyl alcohol and the mixture thereof (cetylstearyl alcohol).

The fatty substance(s) other than the oxyalkylenated fatty amides of formula (I) and other than the oxyalkylenated fatty alcohols, which are preferably solid, can generally represent from 0.1% to 10% by weight, preferably from 0.5% to 8%, more preferably from 1% to 5% by weight, relative to the total weight of the composition according to the invention.

According to one preferred embodiment, the composition according to the invention comprises one or more fatty alcohols other than the oxyalkylenated fatty alcohols, which are preferably solid, in a total content ranging from 0.1% to 10% by weight, preferably from 0.5% to 8%, more preferably from 1% to 5% by weight, relative to the total weight of the composition.

The composition according to the invention preferably comprises a cosmetically acceptable medium. For the purposes of the present invention, the term "cosmetically acceptable medium" is intended to mean a medium that is compatible with keratin fibers, in particular human keratin fibers such as the hair.

The cosmetically acceptable medium of the composition in accordance with the present invention generally comprises water and/or one or more water-soluble organic solvents. Examples of water-soluble organic solvents that may be mentioned include $C_1$-$C_4$ lower alkanols, such as ethanol and isopropanol; aromatic alcohols such as benzyl alcohol or phenoxyethanol; polyols or polyol ethers such as ethylene glycol monomethyl, monoethyl and monobutyl ethers, propylene glycol or ethers thereof such as propylene glycol monomethyl ether, butylene glycol, dipropylene glycol, and also diethylene glycol alkyl ethers, for instance diethylene glycol monoethyl ether or monobutyl ether, or alternatively glycerol; and also mixtures thereof.

The water content generally ranges from 10% to 99% by weight, preferably from 20% to 98% by weight and better still from 50% to 95% by weight relative to the total weight of the composition.

When they are present, the organic solvents are preferably present in proportions of between 0.1% and 20% by weight approximately, relative to the total weight of the oxidizing composition, and even more preferentially between 0.2% and 10% by weight, relative to the total weight of the composition.

The composition in accordance with the invention may also comprise additional compounds conventionally used in cosmetics. These compounds may especially be chosen from thickening or stabilizing polymers, conditioning polymers, especially cationic polymers, chelating agents and fragrances.

Needless to say, those skilled in the art will take care to select this or these optional additional compounds such that the advantageous properties intrinsically associated with the composition in accordance with the invention are not, or are not substantially, adversely affected by the envisioned addition(s).

The composition according to the invention may be in various forms, such as in the form of a cream, a gel or a mousse, or in any other form that is suitable for treating keratin materials, and in particular human keratin fibers such as the hair.

Another subject of the invention is a process for treating keratin fibers, comprising the application to the keratin fibers of an oxidizing composition as defined previously.

The oxidizing composition in accordance with the invention may be used, for example, in a process for dyeing keratin fibers, and in particular human keratin fibers such as the hair.

When the composition of the invention is used for dyeing keratin fibers, this oxidizing composition is employed with a dyeing composition comprising one or more direct dyes and/or one or more oxidation dyes, the oxidizing and dyeing compositions being applied sequentially or simultaneously.

According to one particularly preferred embodiment of the dyeing process, the dyeing composition is mixed, at the time of use, with the oxidizing composition according to the invention. The mixture obtained is subsequently applied to the keratin fibers and left on for approximately 3 to 50 minutes, preferably approximately 5 to 30 minutes, after which the fibers are rinsed, optionally washed with shampoo, rinsed again and dried.

The direct dye(s) may be chosen from the direct dyes conventionally used in direct dyeing. By way of example, these direct dyes are chosen from nitrobenzene dyes, azo direct dyes, methine direct dyes, quinone direct dyes, azine direct dyes, triarylmethane direct dyes, indoamine direct dyes and natural direct dyes. These direct dyes may be of nonionic, anionic or cationic nature.

Among the natural direct dyes that may be used according to the invention, mention may be made of lawsone, juglone, alizarin, purpurin, carminic acid, kermesic acid, purpurogallin, protocatechaldehyde, indigo, isatin, curcumin, spinulosin, apigenidin and orceins. Use may also be made of extracts or decoctions comprising these natural dyes and in particular henna-based poultices or extracts.

The direct dye(s) is (are) generally present in the dyeing composition in an amount of between 0.001% and 20% by weight approximately and even more preferentially between 0.005% and 10% by weight approximately, relative to the total weight of the composition.

The oxidation dye(s) may be chosen from the oxidation bases and couplers conventionally used in the field of dyeing.

Examples of oxidation bases that may be mentioned include para-phenylenediamines, double bases, para-aminophenols, ortho-aminophenols and heterocyclic bases, and the addition salts thereof.

The oxidation base(s) are generally present in the dyeing composition in an amount of between 0.001% and 10% by weight approximately and preferably between 0.005% and 6% by weight approximately relative to the total weight of the composition.

Examples of couplers that may be mentioned include meta-phenylenediamines, meta-aminophenols, meta-diphenols, naphthalene-based couplers and heterocyclic couplers, and the addition salts thereof.

The coupler(s) is (are) generally present in the dye composition in an amount of between 0.001% and 10% by weight approximately and preferably between 0.005% and 6% by weight approximately relative to the total weight of the composition.

In general, the addition salts of the oxidation bases and couplers that may be used in the context of the invention are especially chosen from the addition salts with an acid, such as the hydrochlorides, hydrobromides, sulfates, citrates, succinates, tartrates, lactates, tosylates, benzenesulfonates, phosphates and acetates, and the addition salts with a base, such as sodium hydroxide, potassium hydroxide, aqueous ammonia, amines or alkanolamines.

The oxidizing composition according to the invention may also be used in a process for bleaching or lightening keratin fibers, and in particular keratin fibers such as the hair.

The bleaching composition applied to the keratin fibers may be obtained by mixing an oxidizing composition according to the invention with an aqueous or anhydrous composition preferably containing one or more alkaline agents. The anhydrous composition may be pulverulent or in paste form, and in both cases preferably contains one or more peroxygenated salts, and in particular one or more persulfates. The anhydrous composition in paste form also contains one or more inert organic liquids.

Another subject of the present invention is a process for permanently reshaping keratin fibers, and in particular human keratin fibers such as the hair, using an oxidizing composition as defined above.

According to this process, a reducing composition is applied to the keratin fibers to be treated, the keratin fibers being placed under mechanical tension before, during or after the application of the reducing composition, the fibers are optionally rinsed, the oxidizing composition of the present invention is applied to the optionally rinsed fibers, and the fibers are then optionally rinsed again.

The first step of this process consists in applying a reducing composition to the hair.

The reducing composition comprises at least one reducing agent, which may be chosen in particular from thioglycolic acid, cysteine, cysteamine, glyceryl thioglycolate and thiolactic acid, or thiolactic or thioglycolic acid salts.

The usual step for placing the hair under tension in a shape corresponding to the final shape desired for this hair (for example curls) may be performed by any means, especially mechanical means, which is suitable and known per se for holding the hair under tension, for instance rollers, curlers, combs and the like.

The hair may also be shaped without the aid of external means, simply with the fingers.

Before performing the next optional rinsing step, the head of hair onto which the reducing composition has been applied should conventionally be left to stand for a few minutes, generally between 5 minutes and 1 hour and preferably between 10 and 30 minutes, so as to give the reducing agent enough time to act correctly on the hair. This waiting phase preferably takes place at a temperature ranging from 35° C. to 45° C., while the hair is preferably also protected with a bonnet.

In the second optional rinsing step, the hair impregnated with the reducing composition is rinsed thoroughly with an aqueous composition.

Next, in a third step, the oxidizing composition according to the present invention is applied to the hair thus rinsed, with the aim of fixing the new shape given to the hair.

As in the case of the application of the reducing composition, the head of hair onto which the oxidizing composition has been applied is then, conventionally, left in a standing or waiting phase that lasts a few minutes, generally between 3 and 30 minutes and preferably between 5 and 15 minutes.

If the tension of the hair was maintained by external means, these means (rollers, curlers and the like) may be removed from the head of hair before or after the fixing step.

Lastly, in the final step of the process according to the invention, which is also an optional step, the hair impregnated with the oxidizing composition is rinsed thoroughly, generally with water.

A subject of the present invention is also the use for treating keratin fibers, and in particular human keratin fibers such as the hair, of an oxidizing composition as defined above.

A subject of the present invention is especially the use for dyeing keratin fibers, and in particular human keratin fibers such as the hair, of an oxidizing composition as defined above.

The present invention also relates to using an oxidizing composition as defined above for bleaching or lightening keratin fibers, and in particular human keratin fibers such as hair.

The examples that follow serve to illustrate the invention without, however, being limiting in nature.

EXAMPLE

The following compositions are prepared (amounts in g % of active material).

The compositions are placed in the refrigerator for 2 months at 4° C. and their stability is evaluated visually after a return to ambient temperature.

Compositions A, B and C according to the invention are stable (macroscopically homogeneous and turbid) after 2 months at 4° C.

Composition D, which has a weight ratio of the amount of oxyethylenated fatty alcohol(s) to the amount of oxyethylenated fatty amide(s) of 1.51, is not stable; phase separation occurs a few days after formulation D has been placed in the stability test at 4° C. (translucent lower phase, turbid upper phase).

The same observation was made with regard to composition E which represents a comparative of a formula similar to composition A, but with the oxyethylenated fatty amide of formula (I) according to the invention being replaced in an equivalent amount of active material with an oxyethylenated fatty amide outside the invention. Composition E is not stable; phase separation occurs a few days after formulation E has been placed in the stability test at 4° C. (translucent lower phase, turbid upper phase).

TABLE 1

| | A (invention) | B (invention) | C (invention) | D (comparative) | E (comparative) |
|---|---|---|---|---|---|
| Hydrogen peroxide | 12 | 6 | 1.5 | 12 | 12 |
| Phosphoric acid | qs pH 2.2 ± 0.2 | qs pH 2.2 ± 0.2 | qs pH 2.2 ± 0.2 | qs pH 2.2 ± 0.2 | qs pH 2.2 ± 0.2 |
| Etidronic acid, tetrasodium salt | 0.06 | 0.06 | 0.06 | 0.06 | 0.06 |
| Tetrasodium pyrophosphate. 10 $H_2O$ | 0.04 | 0.04 | 0.04 | 0.04 | 0.04 |
| Sodium salicylate | 0.035 | 0.035 | 0.035 | 0.035 | 0.035 |
| Water | qs 100 | qs 100 | qs 100 | qs 100 | qs 100 |
| Glycerol | 0.5 | 0.5 | 0.5 | 0.5 | 0.5 |
| Oxyethylenated stearyl alcohol (20 OE) | 0.2 | 0.2 | 0.2 | 0.2 | 0.2 |
| (50% linear 70/30 C13/C15)alkyl ether carboxylic acid monoethanolamide (2 OE) | — | — | — | — | 1.016 |
| Oxyethylenated (25 OE) cetylstearyl alcohol | 0.57 | 0.57 | 0.57 | 0.57 | 0.57 |
| Cetearyl alcohol | 2.28 | 2.28 | 2.28 | 2.28 | 2.28 |
| Oxyethylenated rapeseed acid amide (4 OE) | 1.016 | 1.016 | 1.016 | 0.508 | — |
| Weight ratio Oxyethylenated fatty alcohol(s)/oxyethylenated fatty amide(s) | 0.76 | 0.76 | 0.76 | 1.51 | 0.76 |

TABLE 2

| | A (Invention) | B (Invention) | C (Invention) | D (comparative) | E (comparative) |
|---|---|---|---|---|---|
| Stability at 4° C. for 2 months | Stable Macroscopically homogeneous Turbid | Stable Macroscopically homogeneous Turbid | Stable Macroscopically homogeneous Turbid | Not stable Phase separation | Not stable Phase separation |

The invention claimed is:

1. An oxidizing composition comprising:
   at least one oxyalkylenated fatty amide of formula (I) below:

$$R-CO-N(R')-(Alk-O)_nH \qquad (I),$$

wherein:
   R represents an optionally substituted $C_8$-$C_{30}$ alkyl or alkenyl radical;
   R' represents a hydrogen atom or an $(Alk-O)_mH$ radical;
   Alk represents a divalent alkylene radical comprising from 1 to 8 carbon atoms;
   n and m, independently of one another, denote a number ranging from 1 to 50;
   at least one oxyalkylenated fatty alcohol; and
   at least one chemical oxidizing agent;
   wherein the weight ratio of the at least one oxyalkylenated fatty alcohol to the at least one oxyalkylenated fatty amide of formula (I) is less than or equal to 1, and
   wherein the pH of the composition is less than or equal to 5.

2. The composition of claim 1, wherein the at least one oxyalkylenated fatty amide is chosen from oxyethylenated fatty amides of formula (I') below:

$$R-CO-N(R')-(CH_2CH_2O)_nH \qquad (I'),$$

wherein:
   R represents an optionally substituted $C_8$-$C_{30}$ alkyl or alkenyl radical;
   R' represents a hydrogen atom or an $(CH_2CH_2O)_mH$ radical;
   n and m, independently of one another, denote a number ranging from 1 to 50.

3. The composition of claim 1, wherein in formula (I), R' denotes a hydrogen atom, R denotes a $C_{12}$-$C_{22}$ alkyl or alkenyl radical, and n denotes a number ranging from 1 to 50.

4. The composition of claim 1, wherein in formula (I), n denotes a number ranging from 1 to 10.

5. The composition of claim 1, wherein the at least one oxyalkylenated fatty amide is chosen from oxyethylenated rapeseed acid amides.

6. The composition of claim 1, wherein the at least one oxyalkylenated fatty amide is present in an amount ranging from 0.1% to 5% by weight, relative to the total weight of the composition.

7. The composition of claim 1, wherein the at least one oxyalkylenated fatty alcohol is chosen from oxyalkylenated fatty alcohols comprising at least 10 oxyalkylenated units.

8. The composition of claim 1, wherein the at least one oxyalkylenated fatty alcohol is chosen from oxyalkylenated fatty alcohols comprising from 10 to 35 oxyalkylenated units.

9. The composition of claim 1, wherein the at least one oxyalkylenated fatty alcohol is chosen from oxyethylenated fatty alcohols.

10. The composition of claim 1, wherein the at least one oxyalkylenated fatty alcohol is chosen from oxyethylenated stearyl alcohol, oxyethylenated cetyl alcohol, oxyethylenated cetylstearyl alcohol, or mixtures thereof.

11. The composition of claim 1, wherein the at least one oxyalkylenated fatty alcohol is chosen from stearyl alcohol 20 OE and/or cetylstearyl alcohol 25 OE.

12. The composition of claim 1, wherein the at least one oxyalkylenated fatty alcohol comprises at least two different oxyalkylenated fatty alcohols.

13. The composition of claim 1, wherein the at least one oxyalkylenated fatty alcohol comprises at least two different oxyethylenated fatty alcohols.

14. The composition of claim 1, wherein the at least one oxyalkylenated fatty alcohol is present in an amount ranging from 0.1% to 5% by weight, relative to the total weight of the composition.

15. The composition of claim 1, wherein the weight ratio of the total amount of the at least one oxyalkylenated fatty alcohol to the total amount of the at least one oxyalkylenated fatty amide of formula (I) ranges from 0.8 to 0.5.

16. The composition of claim 1, wherein the at least one chemical oxidizing agent is chosen from hydrogen peroxide, urea peroxide, alkali metal bromates, peroxygenated salts, alkali metal or alkaline-earth metal percarbonates, or mixtures thereof.

17. The composition of claim 1, wherein the at least one chemical oxidizing agent is present in an amount ranging from 0.1% to 50% by weight, relative to the total weight of the composition.

18. A process for treating keratin fibers comprising applying an oxidizing composition to the keratin fibers;
   wherein the oxidizing composition comprises:
   at least one oxyalkylenated fatty amide of formula (I) below:

$$R-CO-N(R')-(Alk-O)_nH \qquad (I),$$

wherein:
   R represents an optionally substituted $C_8$-$C_{30}$ alkyl or alkenyl radical;
   R' represents a hydrogen atom or an $(Alk-O)_mH$ radical;
   Alk represents a divalent alkylene radical comprising from 1 to 8 carbon atoms;
   n and m, independently of one another, denote a number ranging from 1 to 50;
   at least one oxyalkylenated fatty alcohol; and
   at least one chemical oxidizing agent;
   wherein the weight ratio of the at least one oxyalkylenated fatty alcohol to the at least one oxyalkylenated fatty amide of formula (I) is less than or equal to 1, and
   wherein the pH of the oxidizing composition is less than or equal to 5.

19. A process for dyeing keratin fibers comprising:
   sequentially or simultaneously applying to the keratin fibers an oxidizing composition and a dyeing composition comprising at least one direct dye and/or at least one oxidation dye;

wherein the oxidizing composition comprises:
at least one oxyalkylenated fatty amide of formula (I) below:

$$R\text{—}CO\text{—}N(R')\text{-}(Alk\text{-}O)_n H \quad (I),$$

wherein:
R represents an optionally substituted $C_8$-$C_{30}$ alkyl or alkenyl radical;
R' represents a hydrogen atom or an $(Alk\text{-}O)_m H$ radical;
Alk represents a divalent alkylene radical comprising from 1 to 8 carbon atoms;
n and m, independently of one another, denote a number ranging from 1 to 50;
at least one oxyalkylenated fatty alcohol; and
at least one chemical oxidizing agent;
wherein the weight ratio of the at least one oxyalkylenated fatty alcohol to the at least one oxyalkylenated fatty amide of formula (I) is less than or equal to 1, and
wherein the pH of the oxidizing composition is less than or equal to 5.

* * * * *